United States Patent [19]

Spears

[11] 4,131,998
[45] Jan. 2, 1979

[54] TUMOR GROWTH MEASUREMENT DEVICE

[76] Inventor: Colin P. Spears, 4901 Oak Terrace Dr., Los Angeles, Calif. 90042

[21] Appl. No.: 775,779

[22] Filed: Mar. 9, 1977

[51] Int. Cl.² .......................... G01B 11/28; G01B 3/14
[52] U.S. Cl. ........................................ 33/1 C; 33/1 V; 33/1 BB; 33/121; 128/2 S
[58] Field of Search ................ 33/1 B, 1 C, 1 V, 1 R, 33/1 F, 1 BB, 121; 128/2 S

[56] References Cited

U.S. PATENT DOCUMENTS

| | | | |
|---|---|---|---|
| 1,780,237 | 11/1930 | Leslie | 33/1 R |
| 2,016,346 | 10/1935 | Smith | 33/121 |
| 2,557,428 | 6/1951 | Grostic | 33/1 C |

Primary Examiner—Richard E. Aegerter
Assistant Examiner—John W. Shepperd
Attorney, Agent, or Firm—William W. Haefliger

[57] ABSTRACT

A device for measuring growth of tumors includes concentric rings on a carrier, the radial spacing of the rings from one another progressively increasing in a radially outward direction.

9 Claims, 2 Drawing Figures

TUMOR GROWTH MEASUREMENT DEVICE

BACKGROUND OF THE INVENTION

This invention relates generally to the measurement of tumor growth, and more particularly to a simple indicator which may be placed over a tumor to measure growth rate.

There is a need for a simple device to measure tumor growth rates in a quick and simple manner. No such device of which I am aware has the simple, highly portable and easily usable configuration as now provided by the present invention.

SUMMARY OF THE INVENTION

It is a fundamental object of the invention to provide a device for measuring growth of tumors, which comprises:
(a) a carrier to be placed over a tumor,
(b) the carrier carrying indicia including spaced marks to delineate tumor growth,
(c) the spacing of successive marks $$R_{n-1}, R_n \text{ and } R_{n+1}$$

characterized in that the space between $R_{n+1}$ and $R_n$ is approximately 1.26 times the spacing between the marks $R_n$ and $R_{n-1}$.

As will be seen, the marks may have concentric ring configuration, so that the center of the rings may be placed over the central visible portion of the tumor; the sheet may be flat or bowed, and may consist of transparent plastic material; it may have circular outline, and designate 18 or 19 rings, or may be square and smaller, designating about 15 rings.

These and other objects and advantages of the invention, as well as the details of an illustrative embodiment will be more fully understood from the following description and drawings, in which:

DRAWING DESCRIPTION

DETAILED DESCRIPTION

Figure 1:
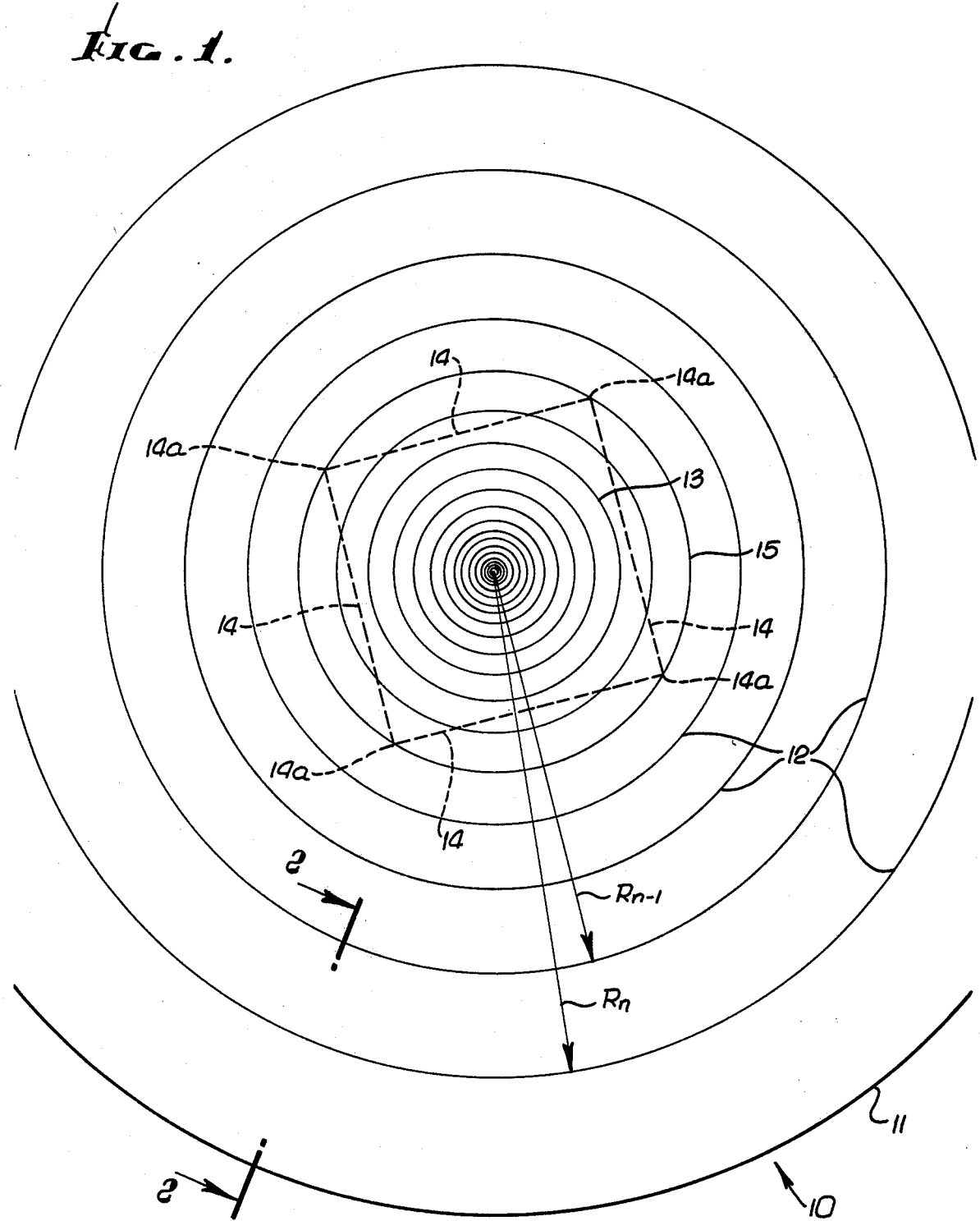
FIG. 1 is a plan view of a device embodying the invention.
Figure 2:
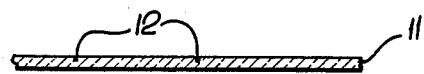
FIG. 2 is a section on lines 2—2 of FIG. 1.

In FIGS. 1 and 2, the device 10 for measuring growth of tumors comprises a translucent sheet 11 to be placed over a tumor, or patient's body lump, or an X-ray photo of a tumor, or any other two-dimensional representation of a tumor. The sheet may advantageously consist of transparent, or nearly transparent plastic material.

The sheet carries a series of concentric rings, or marker circles 12 whereby the center of the rings may be placed over the central visible portion of the tumor, lump, of facsimile thereof. The smallest circle of the group may advantageously be quite small, i.e. less than 1/16 inch in diameter, so that it may be used as a marker and placed over the central portion of the tumor.

An essential feature of the invention is that the radial spacing of the rings is such that the rate of tumor size (or volume) doubling may be approximately determined by temporally sequential mensuration of the tumor, either by directly placing the "Tumor Growth Measurement Device" over the tumor, or over a roentgenographic (X-ray) or any other such two-dimensional representation of the tumor. The radial spacing of the rings in the invention is such that successive rings are expressed as $R_n = 1.26 R_{n-1}$ where $R_{n-1}$ is the approximate radius of a given tumor at time $T_{n-1}$ and $R_n$ is the radius of that tumor at time $T_n$. The time elapsed from $T_{n-1}$ to $T_n$ is that time taken for approximately one tumor size or volume doubling. The value 1.26 is equal to the cube root of 2. For example, if a tumor is found to have changed in size from a ring of radius $R_{n-1}$ to a ring of radius $R_{n+1}$, it follows that the tumor has doubled in volume approximately twice; the average time taken for one tumor volume doubling is thus readily derived:

$$\frac{(T_{n+1}) - (T_{n-1})}{2}$$

It follows that for approximately spherically growing or shrinking tumors, mensuration of the tumor or its X-ray representation, or any other two-dimensional representation, with this invention over time will approximately demonstrate changes in the rate of tumor size (or volume) doubling. This is most particularly applicable to nearly spherical "coin" lesions seen on chest X-ray, round lesions seen on X-ray examination of bones, brain tumors seen on computerized axial tomography, and lymph nodes or other nearly spherical subcutaneous tumors found on medical physical examination.

The sheet 11 preferably has circular outline and a diameter between 4 and 11 inches, and preferably about 10 inches. One of the rings identified at 13 typically has a radius of about 1 inch, and there are at least ten rings (and preferably twelve rings) smaller than ring 13.

Square outline 14 indicates a smaller sheet, or convenient size, which a physician may carry in his pocket. The corners 14a of the square are located at the largest ring 15 subtended by the square outline. The side dimension of the square is about 2¼ inches.

The rings may be dark, suitably inscribed on the sheet, and designated by serial numbers or letters.

I claim:

1. A device for measuring the projected area of a tumor and thus determining volumetric growth of the tumor, comprising,
   (a) a translucent sheet to be placed in registration with a tumor or representation thereof,
   (b) the sheet defining a plane and carrying concentric indicating circles in said plane whereby the center of the circles may be placed in registration with the central visible portion of the tumor or representation, the sheet having a surface and the circles located proximate said surface,
   (c) the radius $R_n$ of each indicating circle "n" being approximately 1.26 times the radius of the next smaller indicating circle, whereby an increase in tumor peripheral size from one of said circles to the next larger circle is indicative of tumor volume doubling.

2. The device of claim 1 wherein the sheet is approximately square, the sheet corners defining a circle concentric to said circles of claim 1.

3. The device of claim 1 wherein one of said circles has a radius of approximately 1 inch, and there are at least ten circles of smaller radius on the sheet.

4. The device of claim 1 wherein said sheet is substantially flat and consists of transparent plastic material.

5. The device of claim 1 wherein said sheet is translucent.

6. The device of claim 1 wherein said sheet has a generally circular outline and has a diameter of between about 4 and 11 inches.

7. The device of claim 6 wherein said diameter is about 10 inches.

8. The device of claim 1 wherein said sheet has a polygonal outline.

9. The device of claim 8 wherein the sheet is approximately square and has a side dimension of about 2¼ inches.

* * * * *